United States Patent [19]

Nakagawa et al.

[11] Patent Number: 4,489,086
[45] Date of Patent: Dec. 18, 1984

[54] SOIL FUNGICIDAL AGENT FOR AGRICULTURE AND HORTICULTURE

[75] Inventors: Taizo Nakagawa, Ageo; Shozo Matsumoto, Omiya; Kaoru Ohmori, Okegawa, all of Japan

[73] Assignee: Nippon Kayaku Kabushiki Kaisha, Tokyo, Japan

[21] Appl. No.: 425,091

[22] PCT Filed: Jan. 29, 1982

[86] PCT No.: PCT/JP82/00028
§ 371 Date: Sep. 16, 1982
§ 102(e) Date: Sep. 16, 1982

[87] PCT Pub. No.: WO82/02648
PCT Pub. Date: Aug. 19, 1982

[30] Foreign Application Priority Data
Jan. 31, 1981 [JP] Japan .................. 56-12246

[51] Int. Cl.$^3$ ............... A01N 47/38; A01N 47/28; A01N 47/22; A01N 47/10
[52] U.S. Cl. .................. 424/273 R; 424/300
[58] Field of Search .................. 424/273 R, 300

[56] References Cited

U.S. PATENT DOCUMENTS

| | | | |
|---|---|---|---|
| 3,755,350 | 8/1973 | Sauli | 424/273 R |
| 3,823,240 | 7/1974 | Sauli | 424/273 R |
| 4,126,696 | 11/1978 | Nakagawa et al. | 424/300 |
| 4,181,519 | 1/1980 | Pilgram et al. | |
| 4,211,785 | 7/1980 | Nakagawa et al. | 424/300 |

FOREIGN PATENT DOCUMENTS

| | | | |
|---|---|---|---|
| 135233 | 10/1975 | Japan . | |
| 0025027 | 2/1977 | Japan | 424/273 R |
| 7508073 | 1/1976 | Netherlands | 424/273 R |

OTHER PUBLICATIONS

S. R. Colby, Weeds, Calculating Synergistic and Anagonistic Responses of Herbicide Combinations, pp. 20-22.

Primary Examiner—Albert T. Meyers
Assistant Examiner—John M. Kilcoyne
Attorney, Agent, or Firm—Banner, Birch, McKie & Beckett

[57] ABSTRACT

A fungicidal composition comprising as effective components, 4-methylsulfonyloxyphenyl-N—methylthiocarbamate:

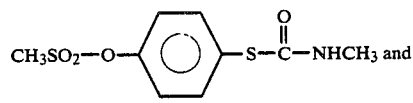

and 1-isopropylcarbamoyl-3-(3,5-dichlorophenyl) hydantoin:

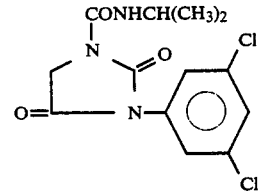

has a synergistic effect and is useful for controlling plant diseases such as damping-off of rice plant seedling, damping-off of cucumber seedling, damping-off disease of cucumber seedling, or brown patch, Pythium patch or rust of turfs.

3 Claims, No Drawings

SOIL FUNGICIDAL AGENT FOR AGRICULTURE AND HORTICULTURE

TECHNICAL FIELD

The present invention relates to a soil fungicidal agent for agriculture and horticulture characterized by comprising as effective components 4-methylsulfonyloxyphenyl-N-methylthiolcarbamate and 1-isopropylcarbamoyl-3-(3,5-dichlorophenyl) hydantion.

4-Methylsulfonyloxyphenyl-N—methyl-thiol-carbamate:

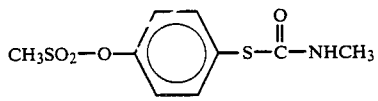

1-Isopropylcarbamoyl-3-(3,5-dichlorophenyl)hydantion:

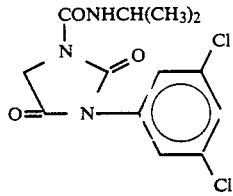

BACKGROUND ART 4-methylsulfonyloxyphenyl-N-methylthiolcarbamate (hereinafter abbreviated to "compound A"), one of the effective components of the present invention is a known compound described in Japanese patent application Kokai (Laid-Open) No. 47527/78. This compound has a broad antimicrobial spectrum and is effective in controlling various soil borne plant diseases on crops and turfs, caused by Fusarium sp., Pythium sp., Rhizopous sp., Phytophthora sp., Trichoderma sp., Rhizoctonia sp., Corticium sp. and the like. However, a sufficient fungicidal effect cannot always be obtained.

1-isopropylcarbamoyl-3-(3,5-dichlorophenyl) hydantion (hereinafter abbreviated to "compound B") is a known compound described in Japanese patent application Kokai (Laid-Open) No. 8097/72, and is developing as a fungicide for controlling gray mold, stem rot and the like. Though compound B is effective against the soil borne plant diseases, caused by Trichoderma sp., Rhizopus sp., Rhizoctonia sp., Fusarium sp., Helminthsporium sp., ; Puccinia sp., sufficient controlling effect cannot be obtained when compound B is used at such a low concentration as to be nonphytotoxic to crops and turfs.

DISCLOSURE OF THE INVENTION

After the inventors have made intensive investigations to develop a fungicide for effectively controlling various soil borne plant diseases such as damping-off of rice plant seedling and cucumber seedling, and brown patch, Pythium patch and rust of turfs and the like, the inventors have found that a composition comprising effective components of compound A and compound B (hereinafter abbreviated to "the present composition") shows a synergistic effect in controlling soil borne plant diseases, as compared to the respective components and moreover exhibits an excellent controlling effect without any phytotoxicity on crops and turfs. The present invention has been completed on the basis of this finding.

Namely, the present composition shows a high controlling effect which is unexpected from the effect of the respective components against the soil borne plant diseases, caused by damping-off of rice plant and cucumber seedlings, brown patch, Pythium patch and rust of turfs at such a low concentration as to give no phytotoxicity on rice plants, vegetables and turfs.

BEST MODE FOR CARRYING OUT THE INVENTION

The weight ratio of compound A to compound B is generally in the range of 8:1 to 1:8, preferably 1:1 to 5:1.

The present composition may be used as a fungicidal composition for agriculture and horticulture as it is or in the form of a mixture with an agricultural adjuvant which improves the effect or which stabilizes the composition depending on the purpose of the use. The composition may be used in the form of, for example, dusts, microgranules, granules, wettable powders, flowable suspension concentrates, ultra low volume compositions or emulsifiable concentrates prepared by a method generally employed in the production of pesticides.

In the practical application, these various types of formulation may be used either as they are or after dilution with water into a suitable concentration.

As agricultural adjuvants herein used, there may be mentioned a carrier (diluent) as well as spreaders, emulsifiers, wetting agents, dispersing agents, binders, disintegrators, etc.

As liquid carriers, there may be mentioned petroleum fractions such as kerosene and light oil, aromatic hydrocarbons such as toluene and xylene, alcohols such as methanol, butanol and glycol, ketones such as acetone, amides such as dimethylformamide, sulfoxides such as dimethylsulfoxide, methylnaphthalene, cyclohexane, animal and vegetagle oils, fatty acids, fatty acid esters, etc.

As soil carriers, there may be mentioned clay, kaolin, talc, diatomaceous earth, silica, calcium carbonate, montmorillonite, bentonite, feldspar, quartz, alumina and sawdust.

As emulsifiers or dispersing agents, surfactants are generally used. They include anionic surfactants, cationic surfactants, nonionic surfactants and amphoteric surfactants such as sodium salts of higher alcohol sulfate, stearyltrimethylammonium chloride, polyoxyethylenealkylphenylethers and laurylbetaine.

These formulations may be used either alone or in the form of a mixture with fungicides, insecticides, plant growth regulators, acaricides, germicides, herbicides, soil modifying agents or nematocides. Further, they may be applied to the soil or locus thereof in the form of a mixture with a fertilizer or another agricultural and horticultural fungicide.

When they are used in the above described forms, the concentration of the compounds used as the effective components in the formulations are varied depending on the forms of the formulations and the agricultural adjuvants used and is generally in the range of 4–95 wt. %.

And preferable content can be given differently for respective types of formulation. For example, in the case of dust, the content of effective components is 4 to 20% and that of adjuvants is 80 to 96%; in the case of emulsifiable concentrate, the content of effective components is 5 to 40% and that of adjuvants is 60 to 95%;

in the case of flowable suspension concentration, the content of effective components is 5 to 40% and that of adjuvants is 60 to 95%; in the case of wettable powder, the content of effective components is 20 to 80% and that of adjuvants is 20 to 80%; and in the cases of granules and microgranules, the content of the effective components is 4 to 10% and that of adjuvants is 90 to 96%.

When the present composition is used in the nursery boxes of rice plants, the content of effective components is used generally in the range of 0.1 to 2.0 g, preferably 0.2 to 1.0 g per nursery box (60 cm long×30 cm wide×3 cm deep).

When the present composition is used in upland field, the content of effective components is used generally in the range of 0.5 kg - 80 kg per hectare.

Then, detailed formulation examples of the present invention will be given below. The kinds of the adjuvants and the mixing ratios should not be limited to the ranges given in the examples but may extend over the ranges.

In the following examples, parts are given by weight.

FORMULATION EXAMPLE 1

Dusts 6 parts of compound A, 4 parts of compound B, 40 parts of talc and 50 parts of clay were mixed together and pulverized to obtained a dust.

FORMULATION EXAMPLE 2

Wettable powders 40 parts of compound A and 30 parts of compound B were mixed with 25 parts of kaolin, 3 parts of sodium salts of higher alcohol sulfate and 2 parts of sodium polyacrylate and the mixture was finely pulverized to obtain a wettable powder.

FORMULATION EXAMPLE 3

Granules 2 parts of previously finely pulverized compound A and 3 parts of previously finely pulverized compound B were mixed with 93 parts of clay and 2 parts of polyvinyl alcohol. 15 parts of water were added to moisten the mixture homogeneously. Then, the mixture was extrusion-molded into granules by means of a granulator. After dressing the granules in a dressing machine, granules having a diameter of 0.6-1 mm were obtained.

FORMULATION EXAMPLE 4

Microgranules 5 parts of previously finely pulverized compound A and 5 parts of previously finely pulverized compound B were homogeneously mixed with 11 parts of clay and 1 part of polyvinyl alcohol to obtain a concentrated powder mixture of the active ingredients. Separately, 78 parts of a non-absorbent coarse mineral powder of 74 to 105 micron size were placed in a proper mixer and then 20 parts of water were added thereto under rotation to moisten the former. The above powder mixture was added thereto to coat the latter with the former. The product was dried to obtain microgranules.

Experimental examples showing the effects of the present invention will be given below.

EXPERIMENTAL EXAMPLE 1

Control test for damping-off of rice plant seedling (caused by Fusarium sp.)

The nursery boxes of 60 cm long, 30 cm wide and 3 cm deep were filled with soil. A wheat bran matrix in which a damping-off fungus (*Fusarium roseum*) was cultured was uniformly inoculated at a rate of 200 g per box. Then, the dust according to the present invention prepared in the same manner as in Formulation Example 1 was added by a predetermined amount and then mixed uniformly with the soil. Then, 0.3 l of rice plant seeds (variety: NIHONBARE) was seeded in stripes in each box. After raising at 32° C. (in an inoculation box) for 3 days, the seeds were held in a chamber which was maintained at 25° C. by day and 20° C. by night for 3 days and next in a room maintained at 3° C. to 5° C. for another 3 days. The boxes were then left in a chamber which was maintained at 20° C. by day and 15° C. by night for 9 days and the state of disease was examined.

The result of the test is shown in Table 1 in terms of "control value" which is calculated as follows:

$$\text{control value} = \frac{\text{good seedling ratio in treated area} - \text{good seedling ratio in untreated area}}{\text{good seedling ratio in treated area}} \times 100$$

where, $$\text{good seedling ratio (\%)} = \frac{\text{number of good seedlings}}{\text{number of examined seedlings}} \times 100$$

TABLE 1

| | Drugs used | Amount of effective component used (g/box) | Control value | Phytotoxicity |
|---|---|---|---|---|
| Control | compound A | 1.0 | 81 | nil |
| | " | 0.5 | 40 | nil |
| | " | 0.25 | 18 | nil |
| | compound B | 1.0 | 50 | observed |
| | " | 0.5 | 38 | nil |
| Present invention | compound A + compound B | 0.5 + 0.5 | 92 | nil |
| | | 0.25 + 0.5 | 76 | nil |

Note:
Compound A: 4-methylsulfonyloxyphenyl-N—methylthiolcarbamate
Compound B: 1-isopropylcarbamoyl-3-(3,5-dichlorophenyl)hydantoin

EXPERIMENTAL EXAMPLE 2

Control test for damping-off rice plant seedling (caused by Rhizopus sp.)

The nursery boxes of 60 cm long, 30 cm wide and 3 cm deep were filled with soil. Then, rice powder soil in which a damping-off fungus (*Rhizopus chinesis*) was cultured was uniformly inculated in the soil at a rate of 500 g per box. Then, the dust according to the present invention prepared in the same manner as in Formulation Example 1 was added by a predetermined amount and mixed uniformly with the soil.

Then, seeds of rice plant (variety: NIHONBARE) was seeded in stripes at a rate of 0.3 l per box, and was raised for 3 days at 35° C. (in an inoculation box) and were left for 3 days in a chamber which is maintained at 25° C. by day and 20° C. by night. Thereafter, the seeds were left in a chamber which is maintained at 20° C. by day and 15° C. by night for 9 days and the state of disease was examined.

The result of the test is shown in Table 2 in terms of control value which is determined as follows:

$$\text{control value} = \frac{\text{good seedling ratio in treated area} - \text{good seedling ratio in untreated area}}{\text{good seedling ratio in treated area}} \times 100$$

where, $$\text{good seedling ratio (\%)} = \frac{\text{number of good seedlings}}{\text{number of examined seedlings}} \times 100$$

TABLE 2

| Drugs used | | Amount of effective components used (g/box) | Control value | Phytotoxicity |
|---|---|---|---|---|
| Control | compound A | 0.5 | 67 | nil |
| " | " | 0.25 | 38 | nil |
| | compound B | 0.5 | 31 | observed |
| " | " | 0.25 | 16 | nil |
| Present invention | compound A + compound B | 0.25 + 0.25 | 87 | nil |

EXPERIMENTAL EXAMPLE 3

Control test for damping-off of rice plant seedling (caused by Trichoderma sp.)

The nursery boxes of 60 cm long, 30 cm wide and 3 cm deep were filled with soil, and a wheat bran matrix in which a damping-off fungus (*Trichoderma viride*) was cultured was uniformly inoculated at a rate of 200 g per box. After the inoculation, the raising was made at 30° C. (in an inoculation box) for 3 days. Thereafter, the test was conducted following the same steps as in Experimental Example 2. The result of the test is shown in Table 3 in terms of control value which is determined as follows:

$$\text{control value} = \frac{\text{good seedling ratio in treated area} - \text{good seedling ratio in untreated area}}{\text{good seedling ratio in treated area}} \times 100$$

where, $$\text{good seedling ratio (\%)} = \frac{\text{number of good seedlings}}{\text{number of examined seedlings}} \times 100$$

TABLE 3

| Drugs used | | Amount of effective components used (g/box) | Control value | Phytotoxicity |
|---|---|---|---|---|
| Control | compound A | 1.0 | 40 | nil |
| " | " | 0.5 | 28 | nil |
| | compound B | 1.0 | 41 | observed |
| " | " | 0.5 | 26 | nil |
| Present invention | compound A + compound B | 0.5 + 0.5 | 64 | nil |

TABLE 3-continued

| Drugs used | Amount of effective components used (g/box) | Control value | Phytotoxicity |
|---|---|---|---|
| compound B | | | |

EXPERIMENTAL EXAMPLE 4

Control test for damping-off of cucumber seedling (caused by Rhizoctonia sp.)

Pots of 12 cm dia. were filled with field soil and pathogenic soil in which a damping-off fungus (*Rhizoctonia solani*) was cultured was inoculated on the surface of the soil at a rate of 5 g per pot uniformly. Then, the dust according to the present invention prepared in the same manner as in Formulation Example 1 was added to and mixed uniformly with the soil. Then, 10 grains of seed of cucumber (variety: OHYASHIMA) were sowed and were made to be attacked with the disease in green house. The state of disease was examined 20 days after the seeding and the good seedling ratio was calculated in accordance with the following equation.

$$\text{good seedling ratio (\%)} = \frac{\text{number of good seedlings in each area}}{\text{number of buddings in the area where neither treatment nor inoculation is made}} \times 100$$

The result of the test is shown in Table 4.

TABLE 4

| Drugs used | Amount of effective component used (g/pot) | Good seedling ratio (%) | Phytotoxicity |
|---|---|---|---|
| compound A | 0.04 | 31 | nil |
| " | 0.02 | 16 | nil |
| compound B | 0.01 | 65 | observed |
| " | 0.005 | 52 | nil |
| compound A + compound B | 0.02 + 0.005 | 74 | nil |

EXPERIMENTAL EXAMPLE 5

Control test for damping-off of cucumber seedling (caused by Phytophthora sp.)

10% dusts according to the present invention pepared in the same manner as in Formulation Example 1 was spread in a predetermined amount over the field where a damping-off fungus (*Phytophthora melonis*) was previously inoculated, and the dusts was mixed uniformly with the surface soil of a thickness of 10 cm.

Then, seeds of cucumber (variety: OHYASHIMA) were sowed.

The state of disease was examined 20 days after the seeding and the good seedling ratio was calculated in accordance with the following equation:

$$\text{good seedling ratio} = \frac{\text{number of good seedlings in each area}}{\text{number of buddings in the area where neither treatment nor inoculation is made}} \times 100$$

TABLE 5

| Drugs used | Amount of effective components used | Good seedling ratio (%) | Phytotoxicity |
|---|---|---|---|
| Compound A | 20 kg/ha | 62 | nil |
| Compound A | 30 kg/ha | 71 | nil |
| Compound B | 15 kg/ha | 5 | nil |
| Compound B | 20 kg/ha | 8 | nil |
| Compound A + Compound B | 20 kg/ha + 15 kg/ha | 98 | nil |
| Compound A + Compound B | 30 kg/ha + 20 kg/ha | 100 | nil |
| Untreated | — | 0 | — |

We claim:

1. An agricultural and horticultural soil fungicidal composition comprising: (i) as the effective components, 4 to 95% by weight of 4-methylsulfonyloxyphenyl-N-methylthiol-carbamate and 1-isopropylcarbamoyl-3-(3,5-dichlorophenyl)hydantoin, the ratio by weight of said carbamate to said hydantoin being in the range of 1:1 to 5:1; and (ii) 5 to 96% by weight of adjuvants.

2. A method for controlling soil borne plant disease caused by fungi selected from the group consisting of Fusarium sp., Trichoderma sp., Rhizopus sp., Phytophthora sp., and Rhizoctonia sp., comprising applying to soil containing said fungi a fungicidally effective amount of a mixture of 4-methyl-sulfonyloxyphenyl-N-methylthiol-carbamate and 1-isopropyl-carbamoyl-3(3,5-dichlorophenyl)hydantoin, the ratio by weight of said carbamate to said hydantoin being in the range of 1:1 to 5:1.

3. The method according to claim 2 wherein said plant disease is selected from the group consisting of damping-off of rice plant seedlings and damping-off of cucumber seedlings.

* * * * *